(12) United States Patent
Walker et al.

(10) Patent No.: US 7,469,032 B2
(45) Date of Patent: Dec. 23, 2008

(54) STRUCTURAL AND PATIENT POSITIONING FEATURES OF AN X-RAY SYSTEM

(75) Inventors: Donald Walker, Mundelein, IL (US); David Pettinato, Schaumburg, IL (US)

(73) Assignee: Gendex Corporation, Washington, DC (US)

( * ) Notice: Subject to any disclaimer, the term of this patent is extended or adjusted under 35 U.S.C. 154(b) by 317 days.

(21) Appl. No.: 11/103,034

(22) Filed: Apr. 11, 2005

(65) Prior Publication Data

US 2006/0227938 A1    Oct. 12, 2006

(51) Int. Cl.
A61B 6/14 (2006.01)
H05G 1/02 (2006.01)

(52) U.S. Cl. .......................... 378/38; 378/195; 378/198

(58) Field of Classification Search .................... 378/37, 378/38, 39, 167, 191, 195–198, 205, 206
See application file for complete search history.

(56) References Cited

U.S. PATENT DOCUMENTS

| | | | |
|---|---|---|---|
| 3,936,641 A | 2/1976 | Heimur | |
| 4,051,379 A | 9/1977 | Zacher, Jr. et al. | |
| 4,060,731 A | 11/1977 | Rissi et al. | |
| 4,181,850 A | 1/1980 | Fairbairn | |
| 4,368,535 A | 1/1983 | Baumann et al. | |
| 4,643,446 A | 2/1987 | Murphy et al. | |
| 4,741,007 A | 4/1988 | Virta et al. | |
| 4,757,968 A | 7/1988 | Kinanen et al. | |
| 4,783,793 A | 11/1988 | Virta et al. | |
| 4,811,372 A | 3/1989 | Doebert et al. | |
| 4,815,115 A | 3/1989 | Nieminen et al. | |
| 4,836,671 A * | 6/1989 | Bautista ...................... 356/3.1 |
| 4,847,881 A | 7/1989 | Heubeck | |
| 4,852,134 A | 7/1989 | Kinanen et al. | |
| 4,856,038 A | 8/1989 | Guenther et al. | |
| 4,974,243 A | 11/1990 | McArdle et al. | |
| 4,985,907 A | 1/1991 | Moteni | |
| D323,892 S | 2/1992 | Spoljaric | |
| 5,157,264 A | 10/1992 | Kinanen et al. | |
| 5,214,686 A | 5/1993 | Webber | |
| 5,272,618 A | 12/1993 | Blake | |
| 5,290,000 A | 3/1994 | Hochstein et al. | |
| 5,340,064 A | 8/1994 | Heimann et al. | |
| 5,355,398 A | 10/1994 | Nakano et al. | |

(Continued)

FOREIGN PATENT DOCUMENTS

EP        0543623 A1    8/1993

(Continued)

*Primary Examiner*—Irakli Kiknadze
(74) *Attorney, Agent, or Firm*—McNees Wallace & Nurick, LLC (57) ABSTRACT

Numerous structural/patient positioning features are provided for use with a dental x-ray machine. At least the following features are included: an inverted motor arrangement to actuate an outer support column with respect to an inner support column; wiper elements disposed between the inner and outer support columns to provide enhanced electrical grounding therebetween; adjustable roller subassemblies disposed between the inner and outer columns; a flexible electrical cable disposed inside the inner column; a self-aligning base for use with the inner column, the base having symmetric halves; an adaptable handgrip handrail extending from the outer column at compound oblique angles; a drive system for film transport; and a side projection system for patient head positioning, including multiple horizontal light beams.

19 Claims, 11 Drawing Sheets

U.S. PATENT DOCUMENTS

| | | | |
|---|---|---|---|
| 5,371,775 A | 12/1994 | Kanerva et al. | |
| 5,384,820 A | 1/1995 | Burke | |
| 5,386,448 A | 1/1995 | Tammisalo et al. | |
| 5,386,449 A | 1/1995 | Wahlstrom | |
| 5,425,065 A | 6/1995 | Jarvenin | |
| 5,431,162 A | 7/1995 | McArdle | |
| 5,511,106 A | 4/1996 | Doebert et al. | |
| 5,530,423 A | 6/1996 | Harrison et al. | |
| 5,579,366 A | 11/1996 | Doebert et al. | |
| 5,590,167 A | 12/1996 | Arai | |
| 5,677,940 A | 10/1997 | Suzuki et al. | |
| 5,708,696 A * | 1/1998 | Kantor | 378/206 |
| 5,921,927 A | 7/1999 | McArdle | |
| D417,503 S | 12/1999 | Spoljaric | |
| 6,118,842 A * | 9/2000 | Arai et al. | 378/39 |
| 6,169,780 B1 | 1/2001 | Yoshimura et al. | |
| 6,173,035 B1 | 1/2001 | Tachibana et al. | |
| 6,431,378 B1 * | 8/2002 | Lewis | 211/151 |
| 6,490,473 B1 | 12/2002 | Katznelson et al. | |
| 6,493,415 B1 * | 12/2002 | Arai et al. | 378/4 |
| D474,542 S | 5/2003 | Malmen | |
| D477,407 S | 7/2003 | Malmen | |
| D478,171 S | 8/2003 | Malmen | |
| 6,722,783 B2 | 4/2004 | Jackson, Sr. | |
| D497,994 S | 11/2004 | Phleps et al. | |
| D502,543 S | 3/2005 | Phelps et al. | |
| 2003/0003776 A1 | 1/2003 | Lohr et al. | |
| 2003/0010182 A1 | 1/2003 | Lohr | |
| 2004/0190678 A1 | 9/2004 | Rotondo et al. | |
| 2004/0202286 A1 * | 10/2004 | Stockl | 378/197 |

FOREIGN PATENT DOCUMENTS

| | | |
|---|---|---|
| JP | 10-174684 A | 6/1998 |

* cited by examiner

FIG.19

STRUCTURAL AND PATIENT POSITIONING FEATURES OF AN X-RAY SYSTEM

FIELD OF THE INVENTION

The present invention is directed to x-ray systems, and more particularly, the present invention is directed to structural and patient positioning features that are used in dental x-ray systems.

BACKGROUND OF THE INVENTION

X-ray systems are commonly used in the dental industry to assist dental professionals. One type of a dental x-ray system uses a diagnostic panoramic technique to take a contiguous radiograph of the entire dentition of the jaw. The panoramic radiograph is achieved by positioning the patient between the x-ray source and a receiving radiosensitive surface. The x-ray source and receiving radiosensitive surface are maintained at a predetermined relationship from each other and revolved around the patient's head while the x-ray beam is continuously directed at the patient. The dental x-ray system contains many moving and non-moving components and is difficult for one person to assemble due to its considerable weight.

What is needed are structural and patient positioning features for use with a dental x-ray device that are inexpensive to manufacture, comfortable to use, provide stability to secure the patient's head position, improve the operation of the dental x-ray device and provide for improved one person assembly of the dental x-ray device.

SUMMARY OF THE INVENTION

The present invention relates to a dental x-ray system including a first substantially vertical column and a second substantially vertical column supporting a dental x-ray device, the second column being movable with respect to the first column. At least one wiper is disposed between the first and second columns, the at least one wiper providing electrical signal grounding between the first and second columns produced by the dental x-ray device.

The present invention further relates to a dental x-ray system including a dental x-ray device for providing a radiograph of a patient's dentition. A positioning device positions the patient's head prior to operating the dental x-ray device, and a projection device projects a plurality of substantially horizontal parallel beams onto the patient's head.

The present invention yet further relates to a dental x-ray system including a substantially vertical column supporting a dental x-ray device. A positioning device is provided for positioning the patient's head prior to operating the dental x-ray device. A handrail adjacent the positioning device provides support for the patient during operation of the x-ray device, the handrail comprising a curved portion extending away from the column, the curved portion being substantially coincident with a plane defining a first oblique angle with a first substantially vertical line. The curved portion has an apex, a second line being coincident with the apex, coplanar with the plane and perpendicular to a tangent line coincident with the apex and coplanar with the plane. Except for the apex of the curved portion, each tangent line to the curved surface extends coplanar to the plane defining a second oblique angle with the second line.

The present invention further relates to a dental x-ray system including a first substantially vertical column and a second substantially vertical column supporting a dental x-ray device, the second column being movable with respect to the first column. At least one pair of opposed roller assemblies is affixed to the second column, each roller assembly interposed between the first and second columns and providing support to the first and second columns along mutually transverse planes.

The present invention still further relates to a dental x-ray system including a first substantially vertical column and a second substantially vertical column supporting a dental x-ray device, the second column being movable with respect to the first column. A motor is connected to the second column, the motor having a threaded shaft extending toward the first column. A threaded sleeve is in threaded engagement with the shaft, the threaded sleeve extending away from the second column. The motor controllably moves the second column with respect to the first column by rotating the shaft with respect to the sleeve.

The present invention still yet further relates to a dental x-ray system including a column supporting a dental x-ray device, the column having a base and a first bracket. A floor mounted second bracket has at least one protrusion formed therein, the base having at least one aperture for receiving the at least one protrusion. A wall mounted third bracket is located substantially vertically above the floor mounting bracket for substantially simultaneously receiving the first bracket while the base is receiving the second bracket.

An advantage of the present invention is that it can be inexpensively manufactured.

A further advantage of the present invention is that it improves patient comfort.

A yet additional advantage is that it secures the patient's head position.

A still further advantage of the present invention is that it improves the operational reliability of the dental x-ray device.

An additional advantage of the present invention is it provides for improved one person assembly of the dental x-ray device.

A still yet further advantage is that it has a concealed flexible electrical cable carrier to accommodate vertical height adjustment of the dental x-ray device of the present invention.

A further advantage is an inverted motor and push rod for raising the outer column, the motor being mounted to the top of the outer column for improved access to the motor of the dental x-ray device of the present invention.

A yet additional advantage is an electrical ground wiper for improved electromotive compatibility of the dental x-ray device of the present invention.

A still further advantage is a separate roller subassembly that is easily installed to the columns of the dental x-ray device of the present invention.

An additional advantage is a self-aligning base to aid in the installation of the dental x-ray device of the present invention.

A still yet further advantage is a tapered self-aligning wall mounted bracket to aid in the installation of the dental x-ray device of the present invention.

A further advantage is a symmetric base that is stackable to minimize storage space and shipping costs of the dental x-ray device of the present invention.

A yet additional advantage is a removable caster assembly to ease one-man installation of the dental x-ray device of the present invention.

A still further advantage is a motor for use with the image capture subassembly that is driven along a separate roller subassembly having components directly coupled to the motor to reduce the number of moving parts of the dental x-ray device of the present invention.

An additional advantage is adaptable handgrip railing to aid with patient positioning associated with use of the dental x-ray device of the present invention.

A still yet further advantage is the provision of multiple horizontal lines to be adaptable to determine the Frankfort plane for differently sized patients of the dental x-ray device of the present invention.

Other features and advantages of the present invention will be apparent from the following more detailed description of the preferred embodiment, taken in conjunction with the accompanying drawings which illustrate, by way of example, the principles of the invention.

BRIEF DESCRIPTION OF THE DRAWINGS

Wherever possible, the same reference numbers will be used throughout the drawings to refer to the same or like parts.

DETAILED DESCRIPTION OF THE INVENTION

Figure 1:
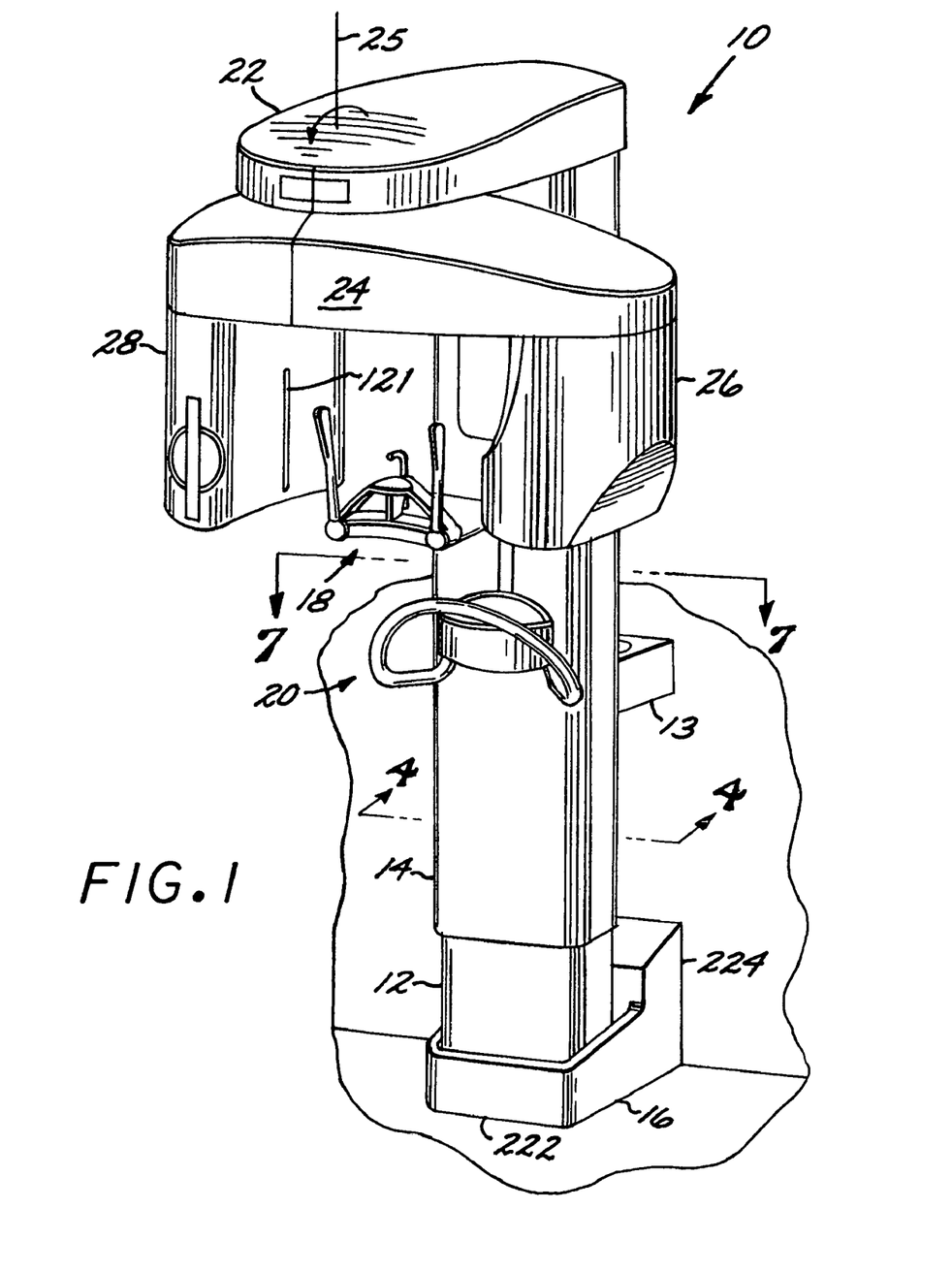
FIG. 1 is a perspective view of a dental apparatus of the present invention.

One embodiment of a dental apparatus 10 of the present invention is depicted in FIG. 1. Preferably, the dental apparatus 10 includes a base 16 in which is set an inner column 12, the inner column 12 extending upwardly from the base 16. An outer column 14 slides along the length of inner column 12 to controllably vary the height of outer column 14 as measured from the floor. A wall-mounted bracket 13 secures inner column 12 in a substantially vertical position. Outer column 14 slidingly supports a handrail 20 and a chinrest 18. Handrail 20 can include one or more bars extending away from outer column 14 in a direction that is ergonomically friendly for a patient (not shown) to grasp while the dental apparatus 10 is in operation. The handrail 20 permits the patient to conveniently stabilize her position once the patient's chin has been placed and positioned on the chinrest 18. Adjacent the end of the outer column 14, a cantilevered member 22 facing away from the floor rotatably carries an inverted U-shaped structure 24 about a substantially vertical axis 25. The U-shaped structure 24 includes a first projection 26 containing an x-ray source and a second projection 28 containing a radiosensitive material or a plurality of radiosensitive receptors or sensors, the projections 26, 28 being connected to and supported by a web 27. During operation of the dental apparatus 10, the projections 26, 28 are rotated about the head of the patient, producing a contiguous radiograph of the entire dentition of the patient's jaw.

Referring to FIGS. 1-2 and 16-17, a base 16 preferably receives inner column 12 to ease positioning of the dental apparatus 10. Base 16 includes a base plate 200 that is supported by and fastened to a backing plate 202. Base plate 200 and backing plate 202 are secured to the bottom of the inner column 12. Preferably, a pair of angles 204 are affixed to the base plate 200 adjacent to a proximal end 206 of the base plate 200, the angles 204 spaced to contact the lower end of the inner column 12 on three sides. To further stabilize the inner column 12, preferably a pair of flanged supports 212 are inserted adjacent to a distal end 210 of the base plate 200 and the inner column 12. One flanged end of each flanged support 212 is secured to the distal end 210 and the other flanged end is secured to the inner column 12. The base plate 200 and backing plate 202 are secured to the floor or wall of a desired location by a floor mounting plate 214. The floor mounting plate 214 preferably is an angle having a pair of perpendicular legs 219. On the leg 219 of the floor mounting plate 214 in contact with the floor, at least one, and preferably two, pins 216 extend upwardly therefrom. At least one aperture 218 is formed in either or both of the legs 219 of the floor mounting plate 214 to receive a fastener to secure the floor mounting plate 214 in position. Once the floor mounting plate 214 is installed, the base 16 can then be secured in position by directing apertures 220 of the backing plate 202 into engagement with the pins 216. To further ease this engagement, either or both of the pins 216 and the apertures 220 can be tapered.

Figure 17:
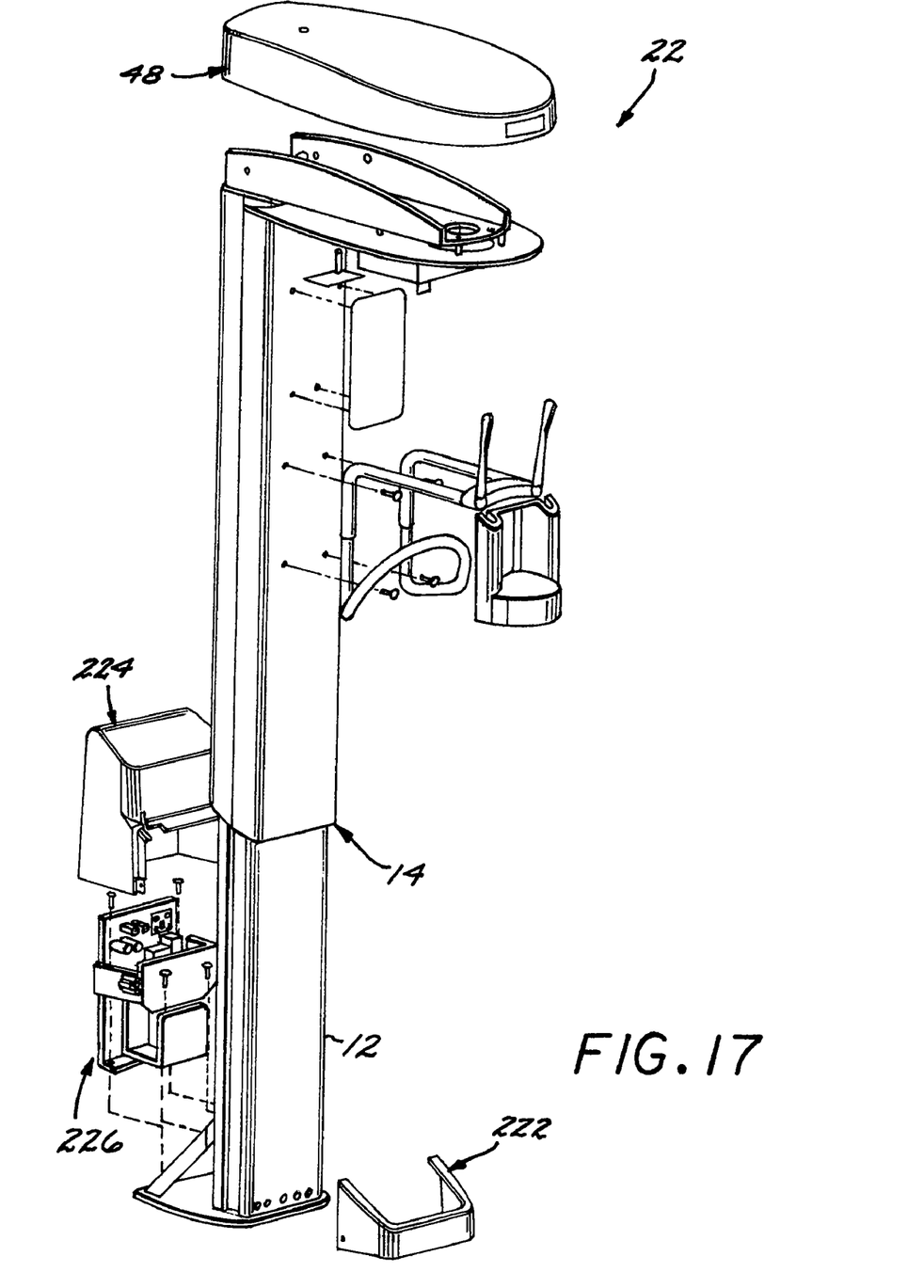
FIG. 17 is a reverse exploded partial view of FIG. 1 of a dental apparatus of the present invention.
Figure 18:
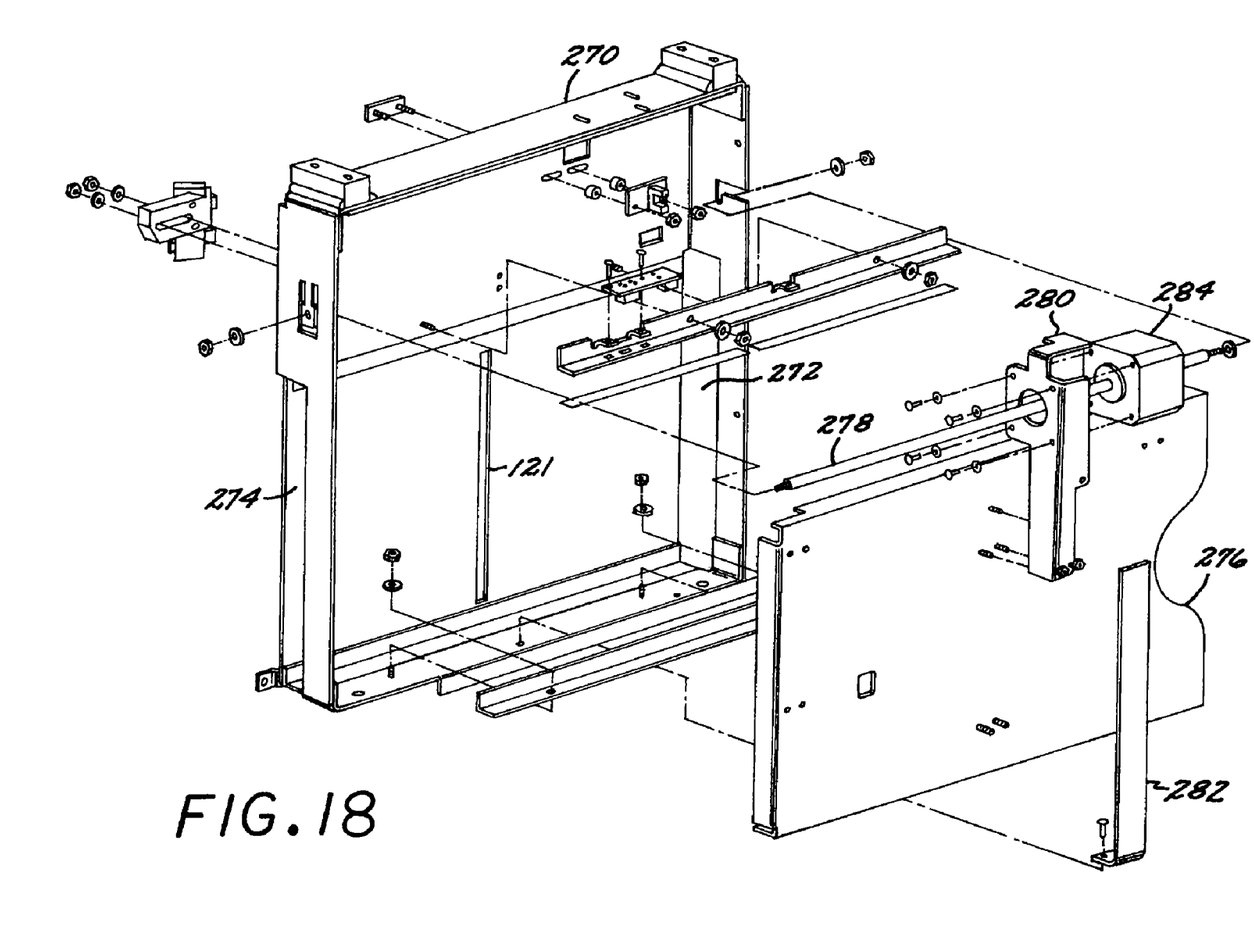
FIG. 18 is an exploded view of components associated with exposing radiographic film to electron beams for a dental apparatus of the present invention.
Figure 19:
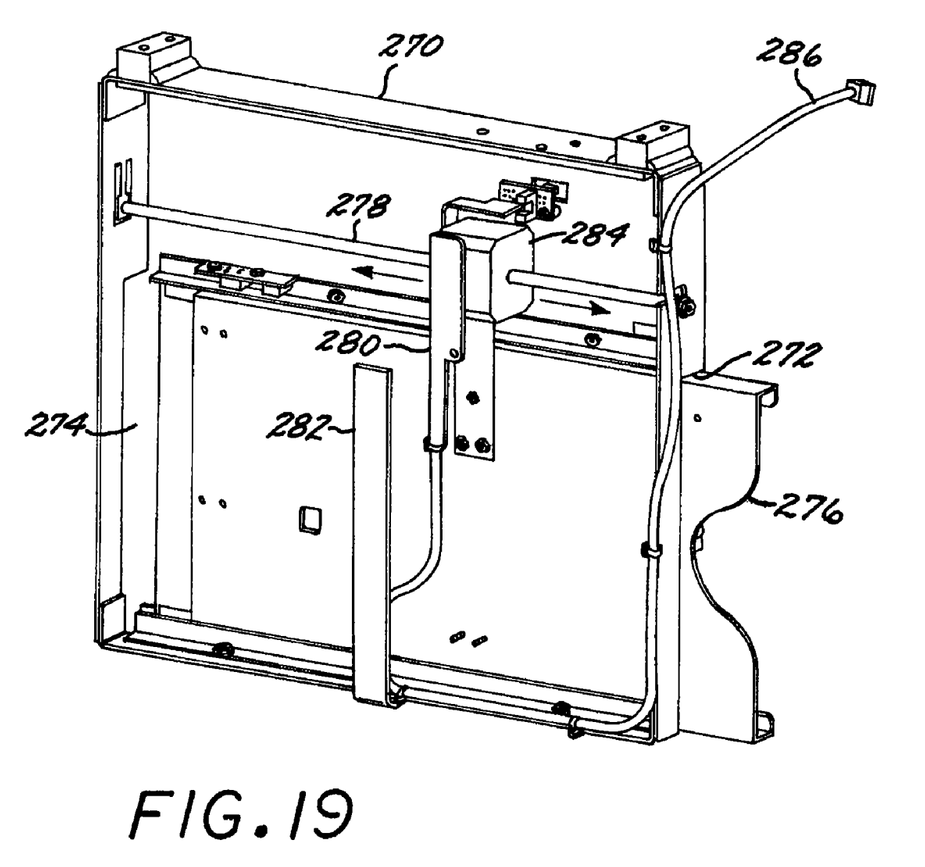
FIG. 19 is an assembled perspective view of the components associated with exposing radiographic film to electron beams from FIG. 18 for a dental apparatus of the present invention.

In a preferred embodiment, as shown in FIG. 17, the base plate 200 and backing plate 202 are hidden from view from exterior of the inner column 12 by a proximal cap 222 and a distal cap 224. Additionally, the distal cap 224 is sized to further hide electrical components 226 from view from exterior of the distal cap 224, the proximal and distal caps 222, 224 providing a pleasing appearance to the dental apparatus 10.

Figure 2:
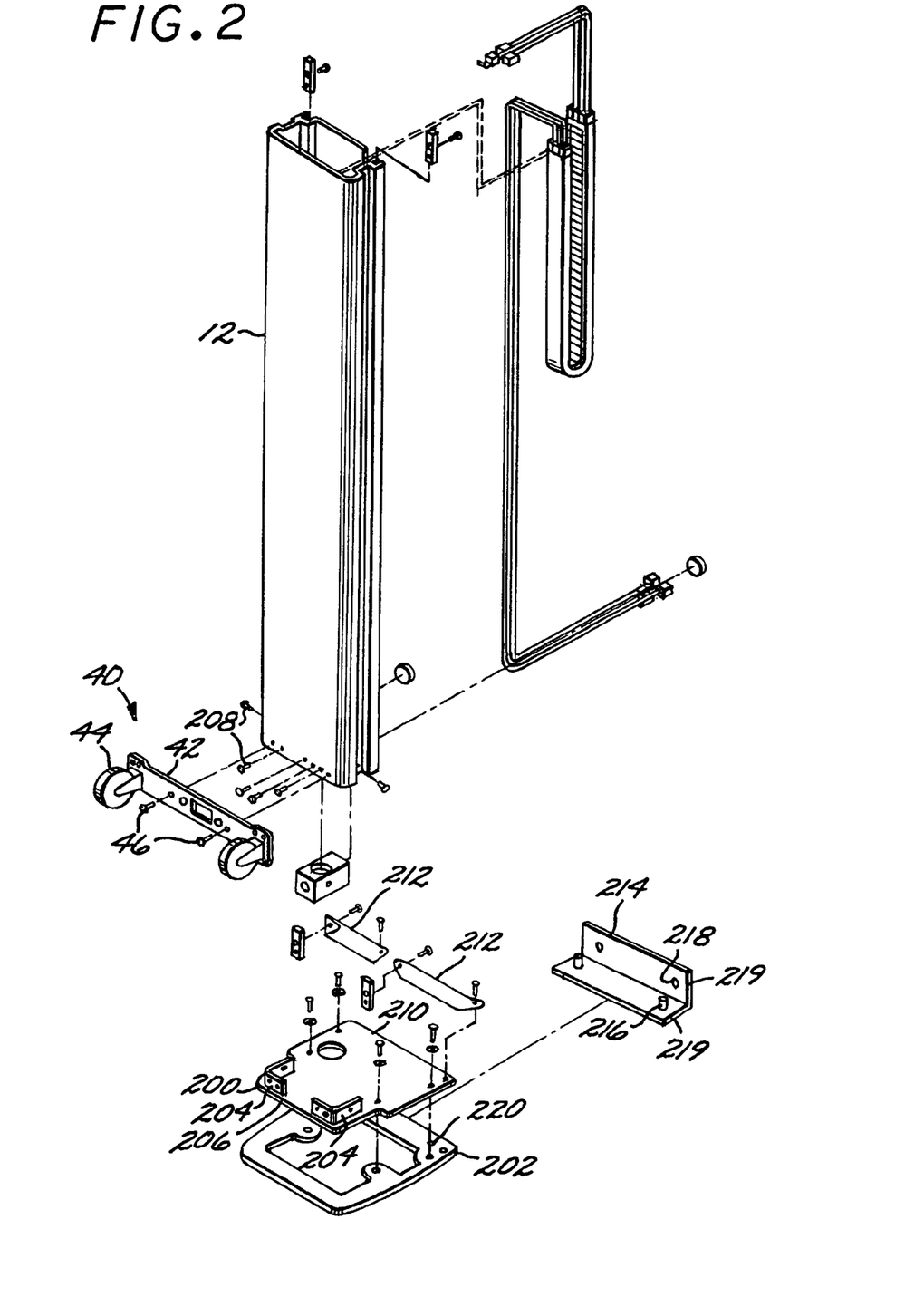
FIG. 2 is an exploded view of an embodiment of a base for a dental apparatus of the present invention.

In a preferred embodiment, such as FIG. 2, the base 16 is symmetric about a vertical plane that is coincident with the midspan of the proximal end 206. Stated another way, the halves of the base 16 define mirror images of each other. Such symmetry is advantageous as it is amenable to compactly arranging multiple bases 16 together, such as by stacking. Benefits from the compact multiple base 16 stacking configurations include reduced shipping and packaging costs as well as a reduced storage space requirement for the bases 16.

Figures 3, 4, 5:
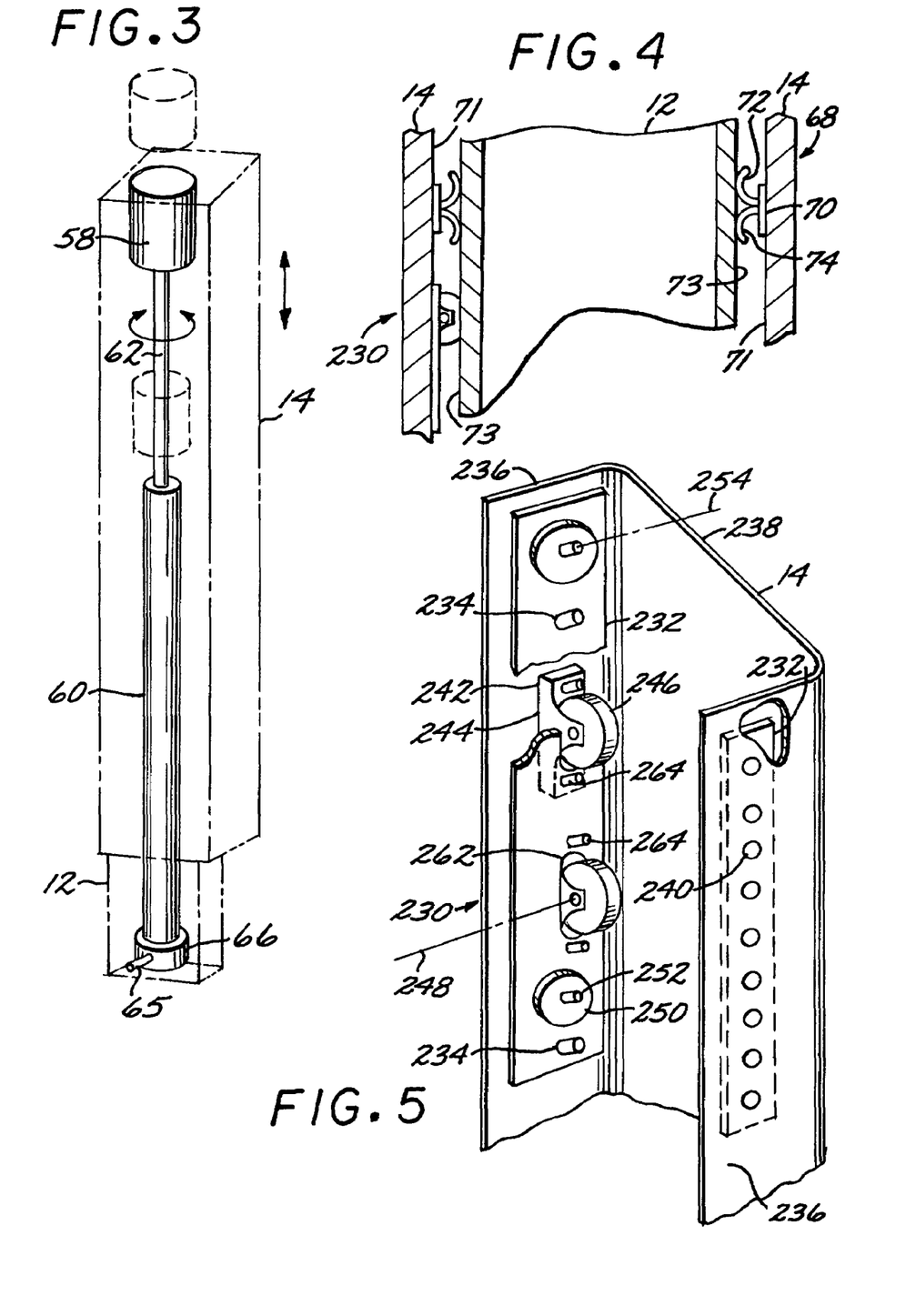
FIG. 3 is a partial perspective view of a motor providing vertical adjustment for a dental apparatus of the present invention.
FIG. 4 is a cross section of an embodiment including grounding wipers and a roller assembly taken along line 4-4 of FIG. 1 for a dental apparatus of the present invention.
FIG. 5 is a perspective view of a roller assembly of the present invention.

Referring to FIG. 3, the orientation of a column motor 58 is now discussed. Motor 58 controls the movement of outer column 14 with respect to inner column 12. Preferably, motor 58 achieves controllable movement of outer column 14 by selectively extending or retracting a threaded shaft 62 with respect to a threaded sleeve 60, which shaft 62 is connected to the motor 58 and is of fixed length. In a preferred embodiment, sleeve 60, which is in threaded engagement with the shaft 62 at one end, extends inside a boss 66 at the other end that is affixed to the base 16 of the inner column 12. Preferably, a pin 65 extends through the boss 66 and into the sleeve 60 to prevent the sleeve 60 from rotating about the axis along its length. Sleeve 60 and shaft 62 support the weight of the outer column 14 and components extending from the outer column 14. Actuating the motor 58 to drive the shaft 62 into rotational movement in one direction decreases the amount of threaded engagement between sleeve 60 and the shaft 62, raising the outer column 14 with respect to the inner column 12. Similarly, actuating the motor 58 to drive the shaft 62 into rotational movement in the other direction increases the amount of threaded engagement between sleeve 60 and the shaft 62, lowering the outer column 14 with respect to the inner column 12.

As the length of shaft 62 is increased by actuation of the motor 58, i.e., the length that shaft 62 extends past the end of sleeve 60, the outer column 14 is similarly raised by an amount equal to the increase in the length of the shaft 62. It is to be understood that motor 58 may be powered by at least one of electrical, hydraulic or pneumatic power from a suitable source (not shown). It is notable that in a preferred embodiment, the motor 58 is secured adjacent to the top of the outer column 14 in an inverted position, providing ease of access for installing or servicing of the motor 58, while minimizing the number of components.

Referring to FIGS. 4-5, grounding wipers 68 preferably each include a base 70 from which an upper wiper element 72 and a lower wiper element 74 outwardly extend. Base 70 is preferably affixed to an inside surface 71 of the outer column 14, the upper and lower wiper elements 72, 74 each extending sufficiently outward to contact a corresponding outside surface 73 of the inner column 12. The spring-like wiper elements 72, 74, which are composed of electrically conductive material, such as a metal, constantly contact or wipe against the inner column 12 at all times, i.e., both while the outer column 14 is stationary with respect to the inner column 12 and while the outer column 14 is moving with respect to the inner column 12. By virtue of the increased surface area contact between corresponding adjacent surfaces 71, 73 of the outer and inner columns 14, 12, the wiper elements 72, 74 provide substantially enhanced electrical grounding contact or electromagnetic compatibility (EMC) filtering between these surfaces. Importantly, this enhanced electrical grounding contact achieves high frequency signal grounding to reduce radiated electromagnetic interference produced by the x-ray system components, providing improved performance by the dental apparatus 10.

Referring to FIGS. 4, 5, 8 and 9, to provide a reduced friction interface between the inner and outer columns 12, 14 and additionally protect the wipers 68 from being crushed or damaged by the corresponding surfaces 71, 73 of the outer and inner columns 14, 12, a pair of opposed roller assemblies 230 can be used. One roller assembly 230 is preferably secured to each opposed outboard side 236 of the outer column 14. As shown in FIG. 5, a front wall 238 of the outer column 14 is removed for clarity. Preferably, a plate 232 is secured to the outboard side 236 by a plurality, such as two, fasteners 234. The heads of the fasteners 234, as well as the other fasteners associated with adjustment of the casters to be discussed in further detail below, are accessible through apertures 240 formed in the outer column 14 from exterior of the outer column 14 for ease of adjustment. Actuating the fasteners 234 in one direction urges the plate 232 away from the outboard side 236. Similarly, actuating the fasteners 234 in the other direction urges the plate 232 toward the outboard side 236.

Figure 8:
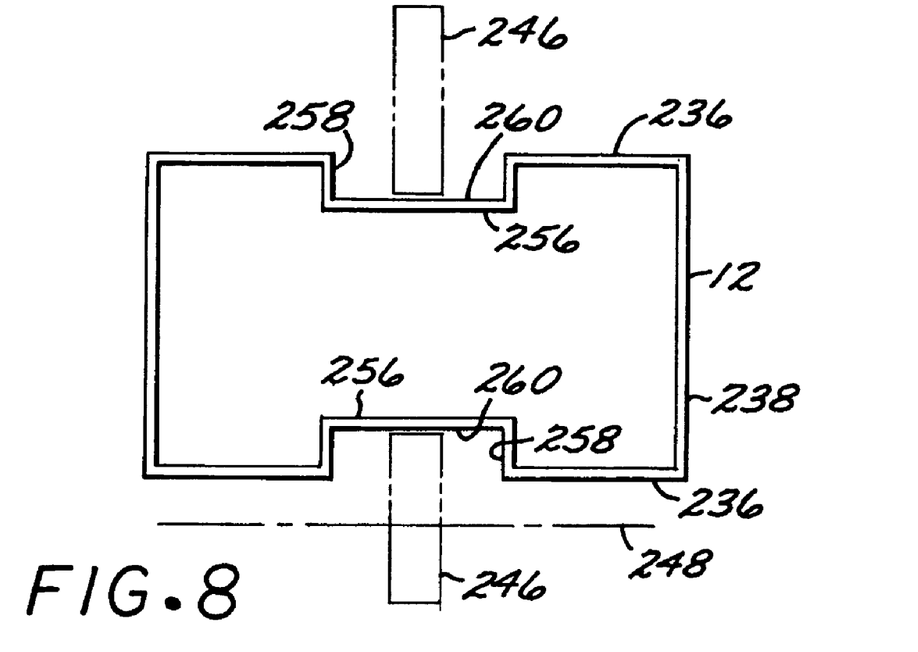
FIGS. 8-9 are cross sections of an embodiment of a caster assembly taken along line 7-7 of FIG. 1 for a dental apparatus of the present invention.

Preferably, there are sets of transversely oriented sets of casters associated with roller assembly 230. The first set of casters is a roller subassembly 242 that includes a frame 244 which is interposed between plate 232 and outboard wall 236 and secured to the plate 232. A portion of the frame 244 extends through a slot 262 formed in the plate 232 and rotatably carries a caster 246 that rotates about an axis 248 which is substantially perpendicular to the rear wall 238 of the outer column 14. A pair of fasteners 264 adjustably secures the frame 244 to the plate 232. That is, activating the head of the fastener 264 in one direction urges the frame 244 toward the plate 232, and similarly, activating the head of the fastener 264 in the other direction urges the frame 244 away from the plate 232. The heads of fasteners 264 are accessible through apertures 240 formed in the outer column 14. Additionally, actuating the frame 244 toward the plate 232 urges the caster 246 toward one of opposed channels 256 formed in the inner column 12. The channel 256 includes a pair of opposed surfaces 258 separated by a recessed surface 260. Thus, the periphery of caster 246 contacts the recessed surface 260 (FIG. 8). It is appreciated by those skilled in the art that opposed sets of casters 246 of opposed roller subassemblies 242 maintain alignment between the inner and outer columns 12, 14 in a plane parallel to the rear wall 238 of the outer column 12.

Figure 9:
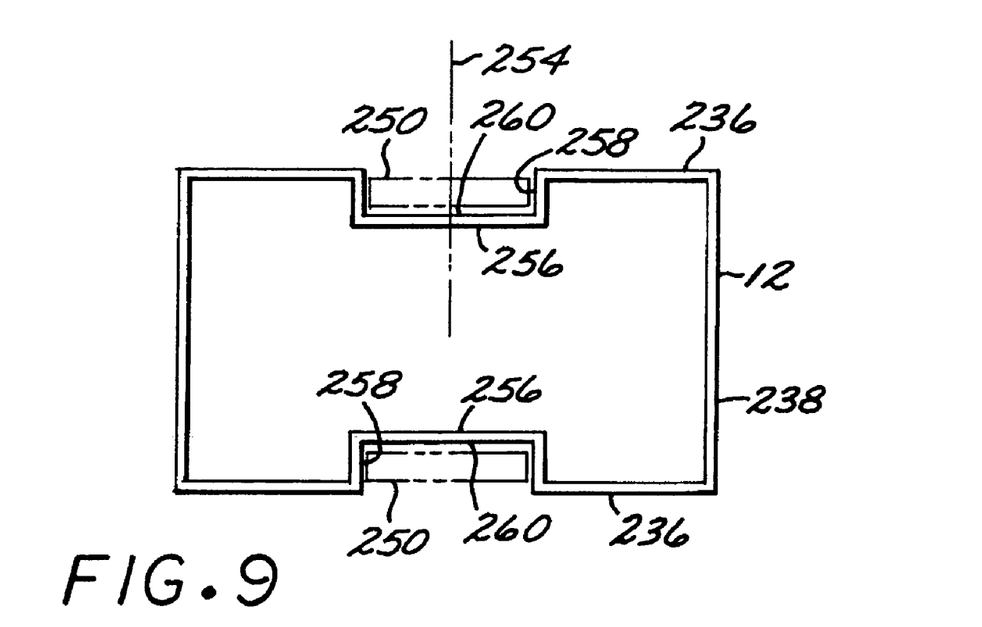
Figure 10:
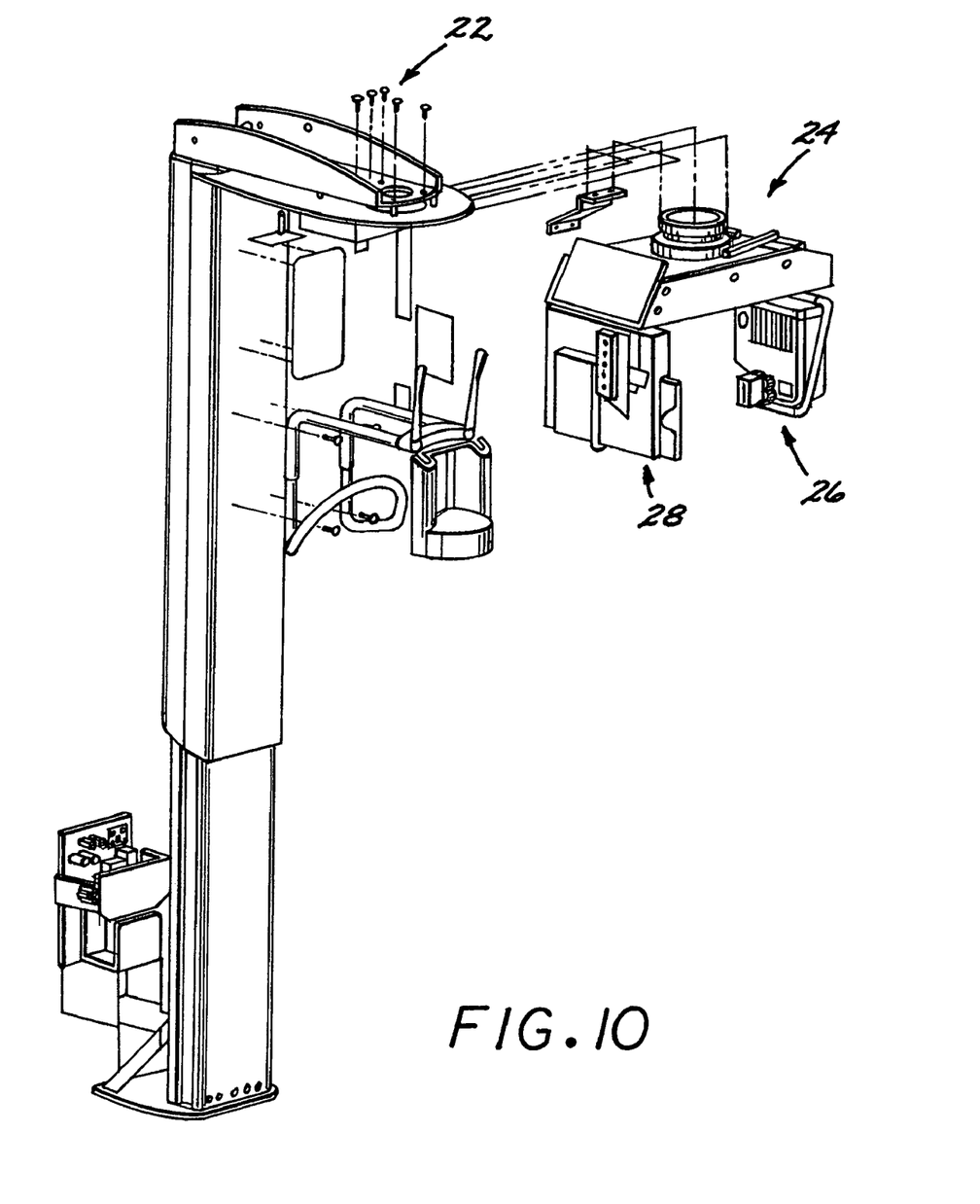
FIG. 10 is an exploded view of a motor and components associated with exposing a radiosensitive surface for a dental apparatus of the present invention.

The other set of casters includes a fastener 252 that rotatably carries a caster 250 about an axis 254, which axis 254 is substantially parallel to rear wall 238 and substantially perpendicular to outboard wall 236. The heads of fasteners 252 are accessible through apertures 240 formed in the outer column 14. Activating the head of the fastener 252 in one direction urges the caster 250 between opposed surfaces 258 of the channel 256 of the inner column 12, and similarly, activating the head of the fastener 252 in the other direction urges the caster 250 away from the opposed surfaces 258 of the channel 256 of the inner column 12. Thus, when the caster 250 is properly installed, the periphery of caster 250 contacts the opposed surfaces 258 of column 12 (FIG. 9). It is appreciated by those skilled in the art that opposed sets of casters 250 maintain alignment between the inner and outer columns 12, 14 in a plane parallel to the outboard walls 236 of the inner column 12. Therefore, caster 250 and caster 246 of roller subassembly 242 provide enhanced stability in mutually transverse planes between the inner and outer columns 12, 14.

Figures 6, 7:
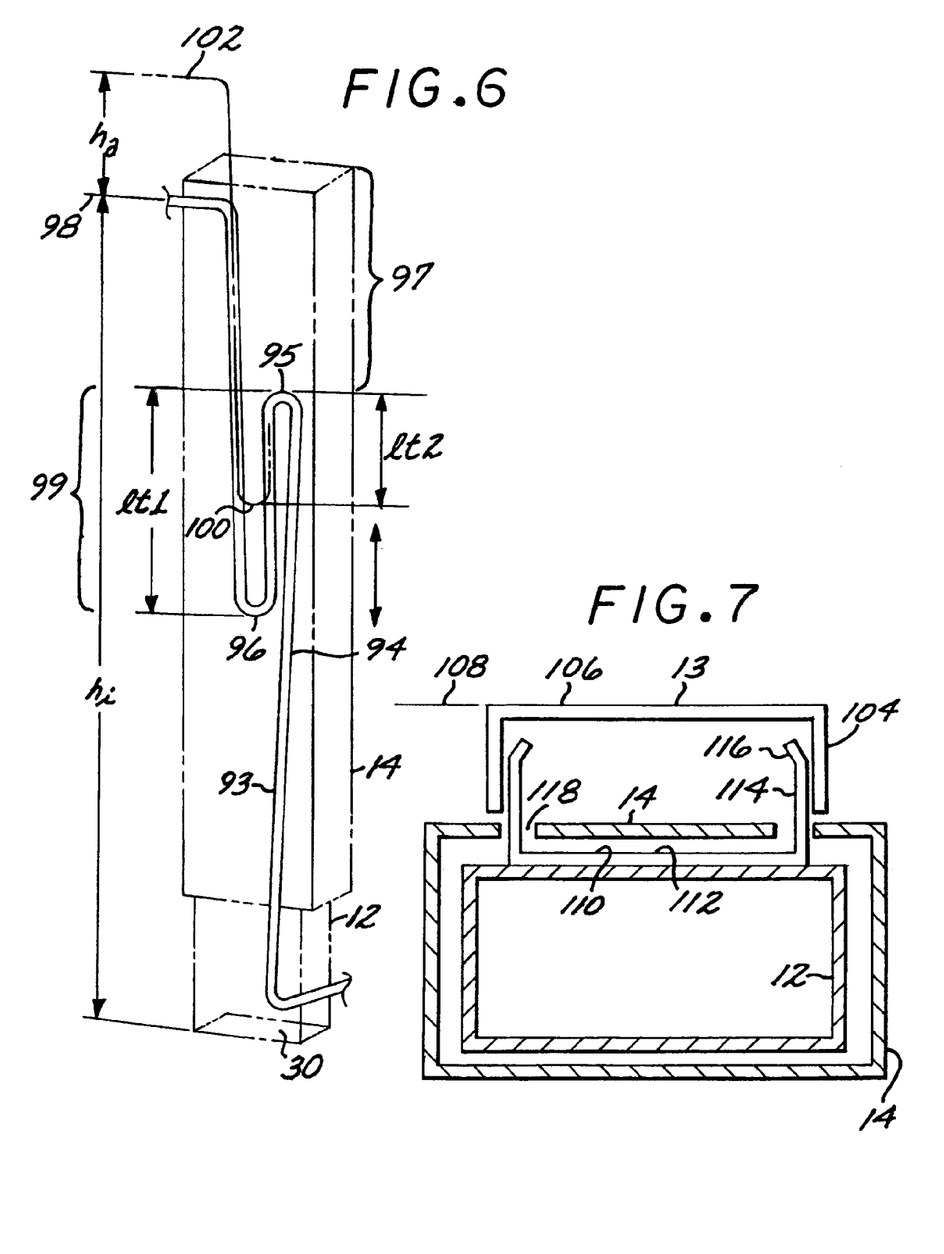
FIG. 6 is a perspective view of an adjustable electrical wiring cable of the present invention.
FIG. 7 is a cross section of an embodiment including a wall bracket having angled arms for supporting the inner column taken along line 7-7 of FIG. 1 for a dental apparatus of the present invention.

Referring to FIG. 6, a flexible electrical cable 94 is inserted inside the inner column 12. The cable 94 is of sufficient length to provide electrical power to the dental apparatus 10 when the outer column 14 is extended to its uppermost position. However, to accommodate for vertical adjustment of the outer column 14 to other positions, the cable 94 preferably defines a lower portion 93 that extends from adjacent the plate 30 adjacent the floor of the room enclosing the dental apparatus 10 to an upper loop 95. Since the upper loop 95 can accommodate the lowest vertical position of the column 14, lower portion 93 does not need to move, therefore the position of the upper loop 95 can be fixed to the inside of the inner column 12 if desired. Similarly, an upper portion 97 of the cable 94 extends between the upper loop 95 and the top of the outer column 14. One end of the upper portion 97 corresponds to the top of the outer column 14 and is fixed, while the other end of upper portion 97 corresponds to the upper loop 95. Thus, while the actual length of the upper portion 97 can vary, it consists of a single substantially vertical run of the cable 94. In other words, the upper portion 97 includes a length of the cable that hangs substantially vertical due to gravity.

Providing the adjustment to the length of the upper portion 97 is a transition region 99 between the upper loop 95 and a lower loop 96. One portion of the transition region 99 is defined by a portion of the cable 94 that extends from lower loop 96 toward the upper loop 95. The other portion of the transition region 99 is defined by a portion of the cable 94 that extends from the lower loop 96 toward the upper portion 97 that is between the lower loop 96 and the upper loop 95. Stated another way, the transition region 99 includes two substantially vertically oriented portions of the cable 94 of equal length (transition length). For example, a change in vertical height from the floor from an initial height 98, referred to as $h_i$, to an added height 102, referred to as $h_a$, must be accounted for by a corresponding change in the transition length, i.e., from an initial transition length, $l_{t1}$ (measured from upper loop 95 to lower loop 96) to a final transition length $l_{t2}$ (measured from upper loop 95 to raised lower loop 100). It can be shown that any increase or decrease in the length of the upper portion 97 ($h_a$) corresponds to a change of the length of the transition region 99 equal to one half of the length change of the upper portion 97. It is to be understood that the position of the upper loop 95 can be adjusted to any position between the floor and the highest position adjacent the top of the outer column 14, which also means that the position of the upper loop 95 can move during vertical adjustment of the outer column 14, and that the transition region 100 can include more than two portions of the cable 94, so long as the cable 94 can provide electrical power to the dental apparatus 10 irrespective of the position of the outer column 14 with respect to the inner column 12. A carrier or guard may be used to ensure the correct cable drape.

By positioning the cable 94 inside the inner column 12, not only is the cable 94 protected from damage by objects exterior of the inner column 12, but substantially all of the cable 94 is hidden from view, which otherwise detracts from the appearance of the dental apparatus 10.

Referring to FIGS. 1, 2 and 7, wall-mounted bracket 13 includes a pair of opposed arms 104 secured at a predetermined spacing by a web 106 to secure the dental apparatus 10 in position to a wall 108. Preferably, each arm 104 is substantially perpendicular to the wall 108. In a preferred embodiment, a bracket 110 is affixed to the inner column 12, slots 118 being formed in the outer column 14 to permit movement of the outer column 14 with respect to the inner column 12 and the bracket 110. Bracket 110 includes a web 112 having opposed arms 114 that extend outwardly therefrom, each arm 114 terminating at an inwardly directed angled portion 116. Bracket 13 is positioned at a predetermined height above the base 16 so that the midspan of the web 106 of the bracket 13 is plumb, or vertically positioned with respect to the midspan of the base 16.

After the bracket 13 has been affixed to the wall 108 plumb to the base 16, the dental apparatus 10 can be easily aligned and installed. The base plate 200 and backing plate 202 secured to the lower end of the inner column 12 are directed into engagement with the floor mounting plate 214, as previously discussed. Simultaneously, the inner column 12 is brought toward the wall 108 into engagement with the bracket 13. The ends of the angled portions 116 of the bracket 110, which are closer together than the distance between the arms 104 of the bracket 13, are directed between the arms 104. The angled portions 116 of bracket 110 received between the arms 104 of bracket 13 are further directed between the arms 104 so that a portion of the arms 114 is also inserted between the arms 104. The arms 114 of bracket 110 are sized to sufficiently engage the arms 104 of bracket 13 so that once the base plate 200 and backing plate 202 are directed into engagement with the floor mounting plate 214, the arms 114, 104 of respective brackets 110, 13 can be secured together by fasteners (not shown). In other words, the angled portions 116 of the bracket 110 provide a self-alignment feature to greatly simplify assembly of the dental assembly 10.

Referring back to FIGS. 1-2, the assembly of the dental apparatus 10, while straightforward, as previously discussed, can be somewhat cumbersome for one-person assembly, due to both the size and weight of the components. To greatly simplify the installation of the inner column 12 into the base 16, as shown in FIG. 2, i.e., eliminate the need to lift and then guide the end of the inner column 12, a removable caster 40 is provided. Preferably, the caster assembly 40 includes a frame 42 configured to rotatably carry a caster 44 adjacent each end of the frame 42. The caster assembly 40 is secured to the lower portion of the inner column 12, such as by fasteners 46. One skilled in the art can appreciate that the caster assembly 40, which preferably includes a pair of casters 44 which are spaced apart from each other, provides a stable rolling platform by which to move the dental apparatus 10, such as directing the dental apparatus 10 into engagement with the floor mounting plate 214 and bracket 110 as previously discussed. Preferably, after the dental apparatus 10 is secured, the caster assembly 40 can be disassembled simply by loosening and removing the fasteners 46 from the inner column 12. Further, in a preferred embodiment as shown in FIG. 17, the disassembled caster assembly 40 can be stored beneath a cover 48 of the cantilevered member 22 for possible future use, such as if the dental apparatus 10 is moved to a different location.

Referring to FIGS. 1, 10, 18 and 19, projection 28 includes components relating to moving the radiographic film during exposure to the electron beam emitted by x-ray components contained in projection 26. Disposed in projection 28 is a housing 270 having an aligned slot 121 formed in the projection 28 and the housing 270 through which electron beams can pass to expose the radiographic film (not shown). Additionally, housing 270 includes aligned openings 272, 274 through which a tray 276 can extend, and a guide 282 to maintain the tray 276 in moving alignment with the openings 272, 274. A threaded rod 278 is secured to the housing 270, a motor 284 being placed in meshing engagement with the threaded rod 278. A housing 280 secures the motor 284 and the tray 276 together so that the housing 280, motor 284 and tray 276 move in unison upon actuation of the motor 284. Actuation of the motor 284 in one direction urges the housing 280, motor 284 and tray 276 to move in unison along the threaded rod 278 toward the opening 274 of housing 270. Similarly, actuation of the motor 284 in the other direction urges the housing 280, motor 284 and tray 276 to move in unison along the threaded rod 278 toward the opening 272 of housing 270. In operation, this movement exposes radiographic film placed in the tray 276 to electron beams passing through slot 121 formed in the housing 270. Preferably, electrical wiring 286 provides electrical power to the motor 284. By virtue of the housing 280, motor 284 and tray 276 moving in unison with respect to the housing 270, the number of components required by the dental apparatus 10 is reduced, as is the space required in projection 28, thereby reducing both the size and expense associated with manufacturing the projection 28 and its associated components.

Figure 15:
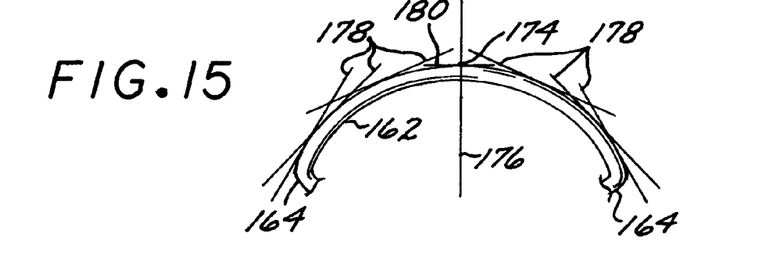
FIG. 15 is a view taken along line 15-15 of FIG. 12 of a handrail of a dental apparatus of the present invention.
Figure 16:
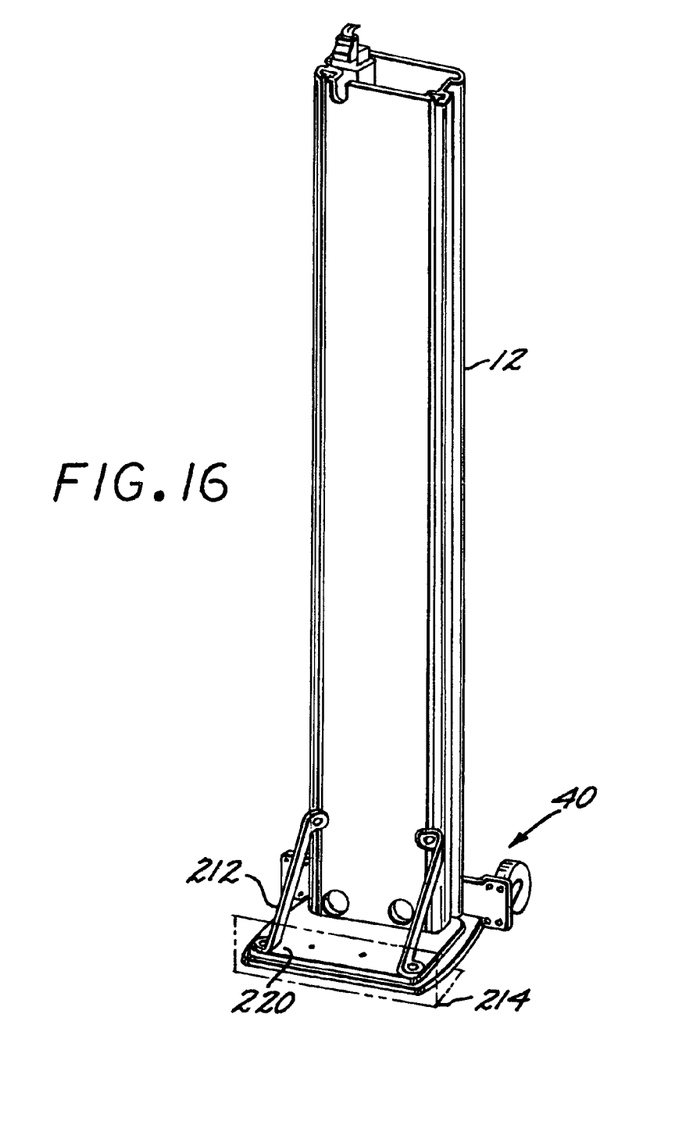
FIG. 16 is a reverse assembled perspective view of FIG. 2 of a dental apparatus of the present invention.

Referring to FIGS. 1, 12-14, handrail 20 provides a symmetric, multiple position handhold for a patient for steadying herself while using the chinrest 18 of the dental apparatus 10. Handrail 20 which is positioned beneath the chinrest 18 includes a curved portion 162 that is substantially coplanar to define a plane which is disposed at an oblique angle 170, preferably an acute angle with respect to the vertical surface of the inner column 12. The midspan of the curved portion 162 includes an apex 174. As shown in FIG. 15, a line 176 is coincident with apex 174 and with the plane defined by the curved portion 162. Line 176 is perpendicular to a line 180 that is tangent to the curved portion 162 and coincident with both apex 174 and with the plane defined by the curved portion 162. As a result, other than apex 174, any line tangent to a point on the curved portion 162 that is coplanar with the plane that is coincident with the curved portion 162, such as 178, defines an oblique angle with line 176, the angle preferably being an acute angle. Stated another way, the angle between lines 178 and 176 decrease in magnitude gradually as the curved portion 162 proceeds toward the elbow portion 164. Therefore, the curved portion 162 provides a continually changing combination of compound oblique angles with respect to the above-identified reference surfaces. By virtue of this continually changing combination of compound oblique angles, a patient can find an especially comfortable position at which to grasp the handrail 20. It is to be understood that since each side of the handrail 20 contains this continually changing combination of compound oblique angles, the patient can grasp the handrail 20 at different positions, each corresponding to a different combination of compound oblique angles, or alternately, can grasp different positions on the same half of the handrail 20 if desired. It is to be understood that the purpose of the handrail 20 is to provide a grasping arrangement for each patient that is ergonomically friendly for that patient, allowing the patient to position herself in a consistent, stable manner in order to achieve the highest quality radiographs.

Figure 11:
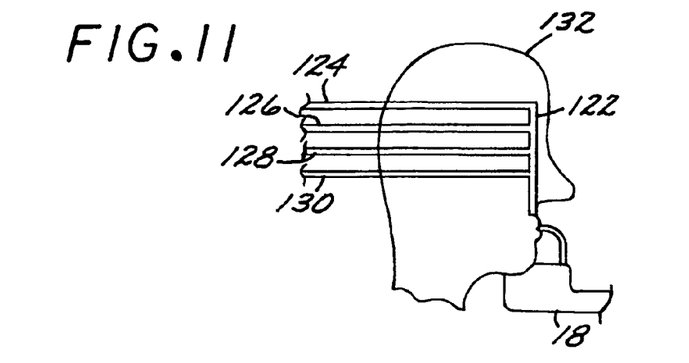
FIG. 11 is an elevation view of projected reference lines onto the side of a patient's face for locating a patient's Frankfort plane for use with a dental apparatus of the present invention.
Figure 12:
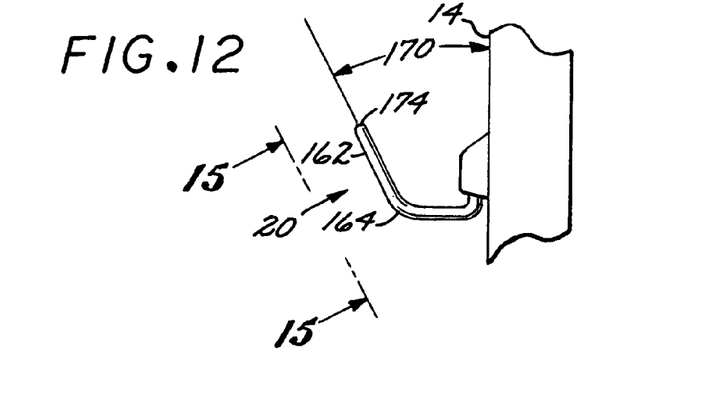
FIGS. 12-14 are differently oriented views of a handrail of a dental apparatus of the present invention.
Figure 13:
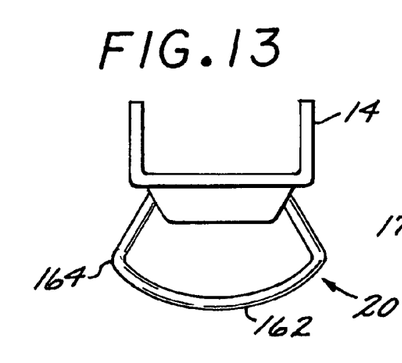
Figure 14:
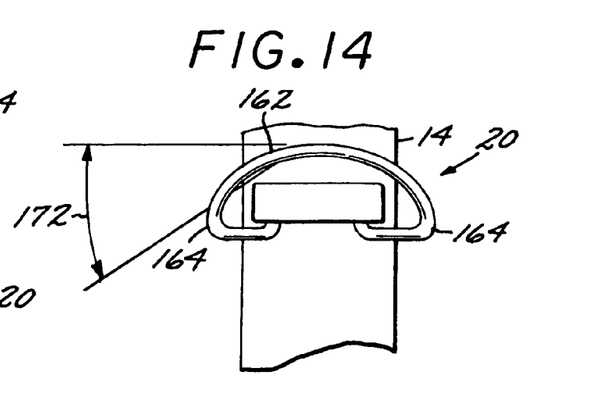

Referring to FIG. 11, a projection technique of the present invention is shown for enhancing patient positioning while the patient's chin is positioned on the chinrest 18, irrespective the size of the patient's head. Typically, a single horizontal light beam is emitted by a light source of a dental apparatus to help provide a reference point for orienting a patient's head prior to processing a radiograph. The patient's reference, referred to as a Frankfort plane, is a line connecting the superior border of the external auditory meatus with the infraorbital rim, as is well known in the art. In a preferred embodiment, as shown in FIG. 11, multiple horizontal light beams 124, 126, 128, 130, as well as a single vertical beam 122 to align with the patient's cuspid, terminating all horizontal beams on the right extent, are emitted by a light source (not shown) of the dental apparatus 10 to help provide a reference point for a patient's head 132 resting on chinrest 18. By virtue of providing the multiple light beams, such as the four shown, or more, if desired, one of the light beams will sufficiently correspond to the Frankfort plane, such as light beam 126 for the patient's head 132 as shown in FIG. 11. Thus, additional adjustment of the projected light beam is not required, saving both time and effort. Further, the light beam projections can originate from an existing cuspid location light (not shown) on the dental apparatus 10, further reducing cost, power usage and the number of components.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A dental x-ray system comprising:
   a first substantially vertical column;
   a second substantially vertical column supporting a dental x-ray device, the second column being movable with respect to the first column; and
   at least one wiper disposed between the first and second columns, the at least one wiper providing electrical signal grounding between the first and second columns produced by the dental x-ray device.

2. The dental x-ray system of claim 1 wherein the at least one wiper include spring-like wiper elements.

3. The dental x-ray system of claim 2 wherein the spring-like wiper elements are composed of electrically conductive material.

4. The dental x-ray system of claim 1 wherein the electrical signal grounding is high frequency signal grounding.

5. A dental x-ray system comprising:
   a dental x-ray device for providing a radiograph of a patient's dentition;
   a positioning device for positioning the patient's head prior to operating the dental x-ray device;
   a projection device projecting a plurality of substantially horizontal parallel light beams onto the patient's head
   a substantially vertical light beam aligned with a patient's cuspid; and
   wherein the plurality of substantially horizontal parallel light beams is emitted from a single source.

6. The dental x-ray system of claim 5 wherein the substantially vertical light beam defines an extent of the substantially horizontal parallel light beams.

7. A dental x-ray system comprising:
   a substantially vertical column supporting a dental x-ray device;
   a positioning device for positioning the patient's head prior to operating the dental x-ray device; and
   a handrail adjacent the positioning device for providing support for the patient during operation of the x-ray device, the handrail comprising a curved portion extending away from the column, the curved portion being substantially coincident with a plane defining a first oblique angle with a first substantially vertical line, the curved portion having an apex, a second line being coincident with the apex, coplanar with the plane and perpendicular to a tangent line coincident with the apex and coplanar with the plane, and except for the apex of the curved portion, each tangent line to the curved surface extending coplanar to the plane defining a second oblique angle with the second line.

8. The dental x-ray system of claim 7 wherein the first oblique angle is an acute angle.

9. The dental x-ray system of claim 7 wherein the second oblique angle is an acute angle.

10. The dental x-ray system of claim 7 wherein the portions of the handrail on each side of the apex are symmetric about the second line.

11. A dental x-ray system comprising:
    a first substantially vertical column;

a second substantially vertical column supporting a dental x-ray device, the second column being movable with respect to the first column; and at least one pair of opposed roller assemblies affixed to the second column, each roller assembly interposed between the first and second columns and providing support to the first and second columns along mutually transverse planes, wherein each roller assembly includes at least one first caster rotatably carried about a first axis and at least one second caster rotatably carried about a second axis transverse to the first axis.

12. The dental x-ray system of claim 11 wherein the first axis and the second axis of each roller assembly are aligned.

13. The dental x-ray system of claim 12 wherein the at least one first caster and the at least one second caster rollably engage a channel formed in the second column.

14. The dental x-ray system of claim 13 wherein the second column includes opposed channels to receive the at least one first and second casters of the at least one pair of opposed roller assemblies.

15. A dental x-ray system comprising:
a first substantially vertical column;
a second substantially vertical column supporting a dental x-ray device, the second column being movable with respect to the first column;
a motor connected to the second column, the motor having a threaded shaft extending toward the first column;
a threaded sleeve in threaded engagement with the shaft, the threaded sleeve extending away from the second column; and
wherein the motor controllably moving the second column with respect to the first column by rotating the shaft with respect to the sleeve.

16. The dental x-ray system of claim 15 wherein the motor is inverted.

17. The dental x-ray system of claim 16 wherein the end of the sleeve opposite the shaft is disposed in a boss adjacent a base of the first column.

18. The dental x-ray system of claim 17 wherein a pin extends through the boss and into at least a portion of the sleeve.

19. A dental x-ray system comprising:
a column supporting a dental x-ray device, the column having a base and a first bracket;
a floor mounted angle having at least one protrusion formed therein, the base having at least one aperture for receiving the at least one protrusion; and
a wall mounted second bracket located substantially vertically above the floor mounted angle for substantially simultaneously receiving the first bracket while the base is receiving the floor mounted angle.

* * * * *